United States Patent [19]

Durbin

[11] 4,003,240
[45] Jan. 18, 1977

[54] CALIBRATION DEVICE FOR VAPORIZED LIQUIDS

[75] Inventor: Damien E. Durbin, Missouri City, Tex.

[73] Assignee: Honeywell Inc., Minneapolis, Minn.

[22] Filed: June 13, 1975

[21] Appl. No.: 586,542

[52] U.S. Cl. .................. 73/1 G; 122/4 R
[51] Int. Cl.² ........................ G01N 31/00
[58] Field of Search ........ 73/1 R, 1 G, 1 F; 122/4

[56] References Cited

UNITED STATES PATENTS

| | | | |
|---|---|---|---|
| 3,592,060 | 7/1971 | Laverman | 73/15 A |
| 3,824,836 | 7/1974 | Lyshkow | 73/1 G |

OTHER PUBLICATIONS

C. P. Hedlin, Materials Research & Standards, Jan. 1966, pp. 25 to 29.

*Primary Examiner*—S. Clement Swisher
*Attorney, Agent, or Firm*—Laurence J. Marhoefer; Lockwood B. Burton; Mitchell J. Halista

[57] ABSTRACT

A calibration device having a thermally insulated storage receptacle for a liquid to be analyzed. The liquid is converted to a vapor form by passing a carrier gas through the liquid to be analyzed whereby the carrier gas is saturated with the liquid. The partial pressure of the liquid vapor in the gas is the function of the temperature of the liquid and the pressure of the saturated carrier gas. The saturated carrier gas is applied to the sample inlet of a vapor phase analyzer by a sample transport line that is maintained above the dew point of the saturated carrier gas. Since the concentration of the calibration liquid in the carrier gas can be precisely calculated by measuring the liquid temperature and the pressure of the saturated carrier gas, the response of the analyzer can be calibrated to this known concentration while maintaining the liquid to be analyzed in a liquid state.

10 Claims, 1 Drawing Figure

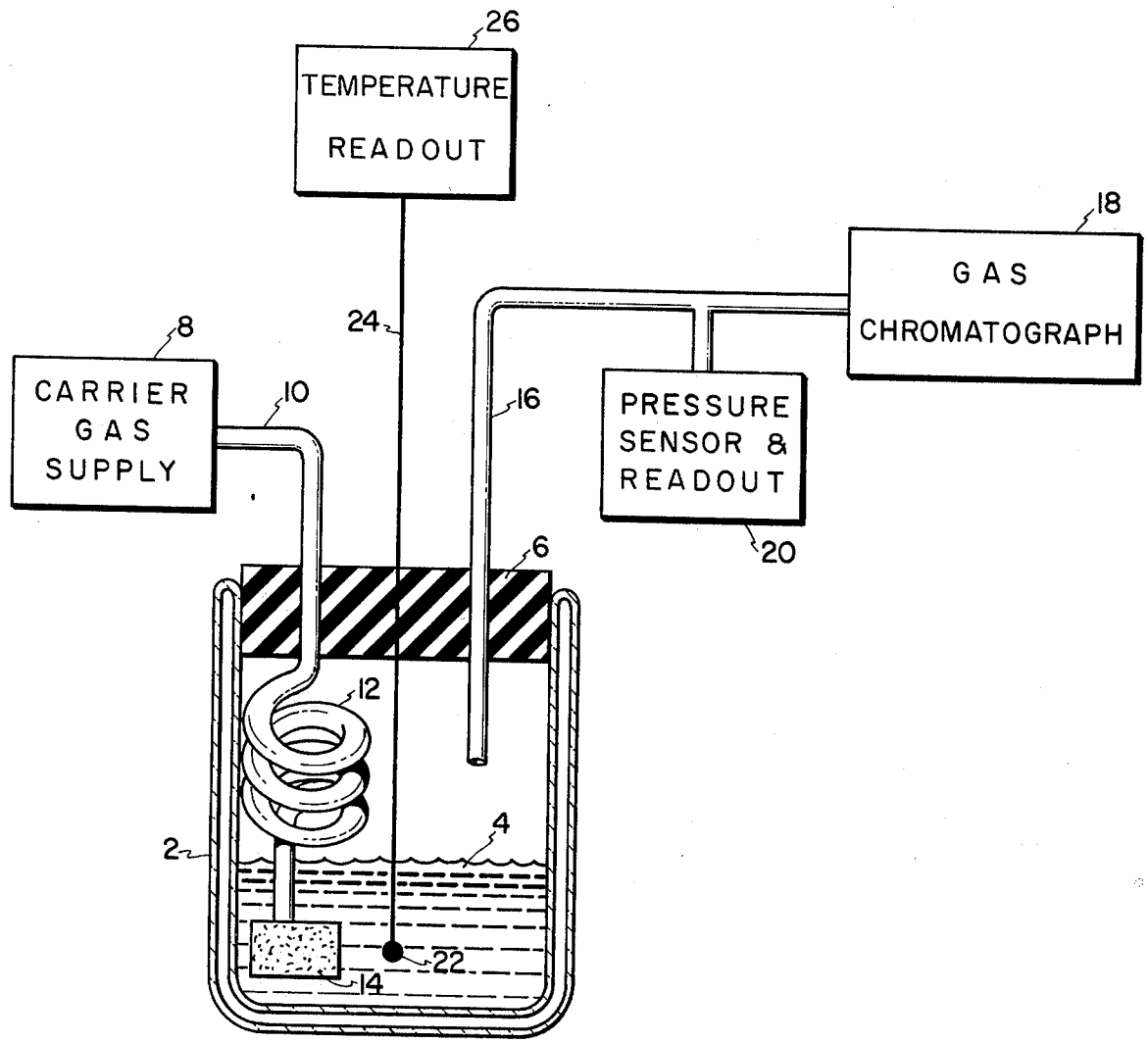

CALIBRATION DEVICE FOR VAPORIZED LIQUIDS

BACKGROUND OF THE INVENTION

1. Field of the Invention

The present invention relates to vapor phase analyzers. More specifically, the present invention is directed to a calibration device for vapor phase analyzers.

2. Description of the Prior Art

Many analytical methods require that the analysis of an unknown substance be performed with the vapor state of the substance, e.g., a gas chromatograph, gas density monitors, combustion monitors, mass spectrophotometers, etc. Such an analytical method usually requires an elevated temperature of the substance to be analyzed to insure complete vaporization of the substance to be analyzed before the vapor is introduced into the gas chromatograph. In other words, if the substance to be analyzed contains components which condense at ambient temperatures the presence of the liquid state render a calibrating operation of an analyzing instrument impractical with ambient temperature operation. This problem is further magnified by the fact that the use of devices for heating the substance to be analyzed, e.g., electrical heaters, is prohibited in many process installations to prevent an explosion of flammable material or other damage to the process and/or analyzing equipment. Thus, the conventional electrochemical methods for calibrating the process analyzer under these conditions would be inconvenient and possibly prohibited.

SUMMARY OF THE INVENTION

An object of the present invention is to provide an improved calibration device for a vapor phase analyzer having means for utilizing liquid samples to be analyzed. Another object of the present invention is to provide an improved calibration device for a vapor phase analyzer utilizing liquid samples and having the capability of being used over a wide range of environmental temperatures while maintaining a compact and portable structure.

In accomplishing these and other objects, there has been provided, in accordance with the present invention, a calibration device for a vapor phase analyzer having a thermally insulated container for storing the liquid sample to be analyzed at a stable temperature and means for equalizing the temperature of the carrier gas with the liquid sample. The carrier gas is subsequently passed through the liquid sample to saturate the carrier gas therewith. The carrier gas saturated with the liquid sample to be analyzed is introduced into a vapor phase analyzer at a measured temperature and pressure whereby the concentration of the sample liquid in the carrier gas can be calculated to calibrate the operation of the vapor phase analyzer.

BRIEF DESCRIPTION OF THE DRAWING

A better understanding of the present invention may be had when the following detailed description is read in connection with the accompanying drawing in which the single FIGURE is a pictorial illustration of a calibration device for a vapor phase analyzer embodying the present invention.

DESCRIPTION OF THE PREFERRED EMBODIMENT

Detailed Description

Referring to the single FIGURE drawing in more detail, there is shown a calibration device for a vapor phase analyzer having a vacuum bottle 2 for storing a sample of a liquid to be analyzed 4 therein. A resilient bottle cap 6 is arranged to close the open end of the vacuum bottle 2 and to allow admittance of inlet and outlet pipe lines and electrical connections therethrough while maintaining a gas tight seal therewith and with the bottle 2, as hereinafter described. A source of a carrier gas 8 is connected by an inlet pipe line 10 passing through the bottle cap 6 to an input of a heat exchanger 12 located within the vacuum bottle 2 above the liquid 4. An output of the heat exchanger 12 is connected to a gas diffuser 14 located beneath the surface of the liquid 4. An outlet pipe 16 passing through the cap 6 has an open end exposed to the interior space of the vacuum bottle 2 above the liquid 4. The other end of the pipe 16 is connected to a vapor phase analyzer such as a gas chromatograph 18 and a pressure sensor 20. A temperature sensor 22 is positioned within the liquid 4 and is connected by an electrical connecting cable 24 passing through the cap 6 to a temperature readout apparatus 26. The outlet pipe 16 may be thermally insulated to maintain its internal temperature above the dew point of the saturated carrier gas.

MODE OF OPERATION

The liquid to be analyzed 4 is initially brought to a desired temperature either prior to being placed within the vacuum bottle 2 or after being stored in the vacuum bottle 2. The cap 6 with the inlet pipe 10, the outlet pipe 16 and the electrical cable 24 passing therethrough is inserted in the open end of the bottle 2 to hermetically seal the liquid 4 therein. The carrier gas from the carrier gas supply 8, which is separate from the carrier gas used in the gas chromatograph 18, is then introduced through the inlet pipe 10 into the liquid 4 by means of the heat exchanger 12 and the gas diffuser 14. The carrier gas is introduced into the liquid at a desired rate, e.g., 10 ml/min. The heat exchanger 12 is effective to bring the carrier gas into thermal equilibrium with the interior temperature of the vacuum bottle 2 prior to the entry of the carrier gas into the liquid 4 through the diffuser 14.

The carrier gas is then passed out of the gas diffuser 14 into the liquid 4 to become saturated with the liquid 4. After the saturated gas leaves the liquid 4, it enters the open end of the outlet pipe 16 to be guided to the gas chromatograph 18. As previously mentioned the entire calibration system can be used in an analyzer oven or other well-known means can be provided to insure that the outlet pipe 16 temperature is above the dew point of the saturated carrier gas. The pressure sensor and readout apparatus 20 and the temperature readout 26 and temperature sensor 22 are used to measure the temperature and pressure of the saturated carrier gas system, respectively, whereby the concentration of the liquid 4 in the carrier gas can be calculated from vapor pressure tables. The vacuum bottle 2 insures that the calibration liquid remains at a constant temperature during the aforesaid calibration procedure. If no restriction to the flow of the saturated carrier gas sample in the outlet line 16 exists downstream of the vacuum bottle 12, the pressure above the liquid 4 in the vacuum bottle 2 can be assumed to be atmospheric. On the other hand, if such a restriction does exist, the saturated carrier gas pressure must be measured on the vacuum bottle side of the restriction to insure that the pressure within the vacuum bottle 2 is being monitored. Thus, the system supplies a carrier gas saturated with the liquid to be analyzed 4 under controlled conditions to provide a known concentration of the liquid with which to calibrate the gas chromatograph 18.

Accordingly, it can be seen that there has been provided, in accordance with the present invention, a calibration device for a vapor phase analyzer for analyzing a liquid sample while maintaining the liquid sample in a liquid state.

The embodiments of the invention in which an exclusive property or privilege is claimed are defined as follows:

1. A vapor phase analyzer system comprising
   thermally insulating means for storing a liquid to be analyzed,
   inlet means for introducing a carrier gas into the liquid to be analyzed in said insulating means,
   vapor phase analyzer means,
   outlet means for applying a saturated carrier gas leaving the liquid to be analyzed to said analyzer means,
   temperature sensor means for measuring the temperature of said liquid to be analyzed within said thermally insulating means, and
   pressure sensor means for measuring the pressure of said saturated carrier gas.

2. A vapor phase analyzer system as set forth in claim 1 wherein said inlet means includes a heat exchanger within said thermally insulating means above the liquid to be analyzed.

3. A vapor phase analyzer system as set forth in claim 2 wherein said inlet means includes a gas diffuser located within said liquid to be analyzed and said outlet means includes a thermally insulated gas line for maintaining the saturated carrier gas above its dew point between said thermally insulating means and said vapor phase analyzer means.

4. A vapor phase analyzer system as set forth in claim 3 wherein said thermally insulating means includes a vacuum bottle and bottle cap means for sealing said bottle while admitting said inlet means, said temperature sensor means and said outlet means.

5. The method of operating vapor phase analyzer system including the steps of storing a liquid to be analyzed within a thermally insulated container, passing a carrier gas through the liquid, guiding a carrier gas leaving the liquid to a vapor phase analyzer, measuring the temperature of the liquid and measuring the pressure of the carrier gas leaving the liquid.

6. A method as set forth in claim 5 and including the further step of passing the carrier through a gas diffuser before the carrier gas enter the liquid.

7. A method as set forth in claim 6 and including the further step of passing the carrier gas through a heat exchanger located above the liquid before the carrier gas enters the gas diffuser.

8. A carrier gas saturating device comprising
   thermally insulating means for storing a liquid to be analyzed,
   inlet means for introducing a carrier gas into the liquid to be analyzed in said insulating means,
   outlet means for applying a saturated carrier gas leaving the liquid to be analyzed to an outlet port,
   temperature sensor means for measuring the temperature of said liquid to be analyzed within said thermally insulating means, and
   pressure sensor means for measuring the pressure of said saturated carrier gas.

9. A carrier gas saturating device as set forth in claim 8 wherein said inlet means includes a heat exchanger within said thermally insulating means above the liquid to be analyzed and a gas diffuser located within said liquid to be analyzed and said outlet means includes a thermally insulated gas line between said thermally insulated means and said port for maintaining said saturated carrier gas above its dew point.

10. A carrier gas saturating device as set forth in claim 9 wherein said thermally insulating means includes a vacuum bottle and a bottle cap means for sealing said bottle while admitting said inlet means, said temperature sensor means and said outlet means.

* * * * *